United States Patent [19]
Pyles

[11] Patent Number: 6,149,899
[45] Date of Patent: Nov. 21, 2000

[54] OPAQUE CONDITIONING COMPOSITION

[75] Inventor: Daniel Raymond Pyles, Chicago, Ill.

[73] Assignee: Helene Curtis, Inc., Chicago, Ill.

[21] Appl. No.: 09/130,955

[22] Filed: Aug. 7, 1998

[51] Int. Cl.$^7$ ..................................................... A61K 7/075
[52] U.S. Cl. ........................................ 424/70.28; 424/70.1
[58] Field of Search ................................ 424/70.1, 70.28

[56] References Cited

U.S. PATENT DOCUMENTS

| | | |
|---|---|---|
| 4,678,475 | 7/1987 | Hoshowski et al. . |
| 4,976,956 | 12/1990 | Noe . |
| 5,114,706 | 5/1992 | Duvel . |
| 5,271,926 | 12/1993 | Kure et al. . |
| 5,747,436 | 5/1998 | Patel et al. . |

FOREIGN PATENT DOCUMENTS

| | | |
|---|---|---|
| 0130609 | 1/1985 | European Pat. Off. . |
| 4425096 | 2/1995 | Germany . |
| 56/169613 | 5/1980 | Japan . |
| 56/169614 | 5/1980 | Japan . |
| 56/169615 | 5/1980 | Japan . |
| 56/169617 | 5/1980 | Japan . |
| 2316615 | 3/1998 | United Kingdom . |

Primary Examiner—Thurman K. Page
Assistant Examiner—Amy E. Pulliam
Attorney, Agent, or Firm—Matthew Boxer

[57] ABSTRACT

The present invention relates an opaque conditioner which comprises a monoalkyl quat from C16 to higher Carbon chain lengths (preferably C16 to C22) and a dialkyl quat from C20 to C22. Also included is an amount of fatty alcohol necessary to opacify the conditioner. The monoalkyl quat is necessary in a ratio to the dialkyl quat of about not less than 4:1. The fatty alcohol is present in an amount from about 1% to about 4%.

3 Claims, No Drawings

OPAQUE CONDITIONING COMPOSITION

BACKGROUND OF THE INVENTION

Most individuals buy and use a hair shampoo for its cleansing properties. In addition to having clean hair, a consumer also desires sufficiently-conditioned hair that holds a preset configuration. However, hair shampoos generally are formulated with highly effective anionic surfactants that primarily clean as opposed to conditioning in the hair. Anionic surfactants not only remove the dirt and soil from the hair, but also remove sebum naturally present on the surface of the hair fibers. Therefore, the desirable cleansing properties of anionic surfactants also leave the hair in a cosmetically-unsatisfactory condition. Shampoos also do not detangle wet hair and do not impart residual conditioning benefits to dry hair, such as manageability or styleability of hair sets.

In general, shampoo compositions containing anionic surfactants, or nonionic surfactants or amphoteric surfactants, leave hair with an undesirable harsh, dull and dry touch, or feel, usually called "creak", after the hair is shampooed and then rinsed with water. Furthermore, thoroughly cleansed hair also is extremely difficult to comb, in either the wet or the dry state, because the individual hair fibers tend to snarl, kink, and interlock with each other. In addition, incompletely dried hair, such as hair dried with a towel, has poor brushing properties, and after complete drying, the hair does not set well. The combing or brushing property of dry hair remains poor, and the hair has undesirable electrostatic properties in a low humidity atmosphere that causes the hair to "fly away", thereby further reducing the brushing properties of the hair.

The unsatisfactory combing or brushing property of hair immediately after shampooing, or during trimming treatments after shampooing, also causes hair damage, such as split ends or hair breakage. In addition, the natural luster and resiliency of the hair is reduced. The overall unsatisfactory condition of shampooed hair often necessitates a subsequent post-shampoo treatment of the hair with a conditioning composition to improve these undesirable physical characteristics. Conditioning compositions typically are applied separately from the hair shampoo, and usually are rinses, cream-like emulsions or lotions containing a cationic compound.

Therefore, consumer needs traditionally have been met by the application of a shampoo to cleanse the hair, followed by the application of a conditioner composition to improve wet combing. The commonly accepted method has been to shampoo the hair, followed by rinsing the hair, and then separately applying a conditioner composition, followed by a second rinse. The wet combing problem has been solved by treating shampooed hair with a conditioner composition that coats the hair shaft and causes the individual hair shafts in a tress to resist tangling and matting because of the conditioner residue retained on the shaft.

However, the need for improved compositions that condition the hair, i.e., render the hair more manageable, has long been recognized in the art. As previously discussed, it is well-known that anionic surfactants are suitable for hair shampooing, and that cationic compounds, like cationic surfactants and cationic polymers, are useful as hair conditioners. Therefore, cationic compounds that are substantive to hair often are used to complete the hair cleansing and hair conditioning cycle.

The ability of cationic compounds to adsorb to or interact with the keratinous material of the hair makes these compounds desirable for improving wet hair detangling and dry hair manageability. However, cationic compounds that adsorb particularly strongly to the hair also can reduce the elasticity, body and set of the dried hair. Therefore, although conditioning compositions for application to freshly shampooed hair are well known, new and improved conditioning formulations based on cationic compounds are continually sought.

The following is a list of patents in this field.
JP 56169617 A
JP 56169615 A
JP 87008088 B
JP 56169614 A
JP 87008087 B
JP 56169613 A
JP 87008086 B
and U.S. Pat. No. 4,976,956.

The present invention is directed to a new opaque conditioning composition that is esthetically acceptable to consumers, improves the wet combing and dry combing properties of hair, and also leaves the dry hair with satisfactory cosmetic and physical properties, including, in particular, dry combing and feel, less hair coating, manageability, body, condition of the ends and set.

SUMMARY OF THE INVENTION

The invention is an opaque conditioner that has a combination of two different types of conditioning agents and an emulsifier. The present invention is a low solids formulation that provides substantial conditioning benefit without compromising viscosity to users who use conditioners.

The purpose of the invention is to provide a conditioner with improved performance, while using effective materials at ratios that maximize their benefit.

The present invention relates an opaque conditioner which comprises a monoalkyl quat from C16 to higher Carbon chain lengths (preferably C16 to C22) and a dialkyl quat from C20 to C22). Also included is an amount of fatty alcohol necessary to opacify the conditioner. The monoalkyl quat is necessary in a ratio to the dialkyl quat of about not less than 4:1. The fatty alcohol is present in an amount from about 1% to about 4%.

Another aspect of the invention is to provide a method of treating the hair to yield well-conditioned hair having esthetically pleasing physical properties by contacting the hair with an opaque conditioner of the present invention.

DETAILED DESCRIPTION OF THE INVENTION

Unless indicated otherwise, as used herein, % means weight %.

The present invention relates an opaque conditioner which comprises a monoalkyl quat from C16 to higher Carbon chain lengths (preferably C16 to C22) and a dialkyl quat from C20 to C22. Also included is an amount of fatty alcohol necessary to opacify the conditioner. The monoalkyl quat is necessary in a ratio to the dialkyl quat of about not less than 4:1. The ratio of monoalkyl quat to dialkyl quat can range from about 4:1 to about 5:1; or from about 4:1 to about 10:1; or from about 4:1 to about 20:1. Fatty alcohol is present in an amount from about 1% to about 4%.

Monoalkyl quats can be compounds of the formula $N^+R^1 R^2 R^3 R^4 X^-$ wherein $R^1$, $R^2$, and $R^3$ are C1–C3 alkyl groups and $R^4$ is a C16 or higher alkyl group; and X⁻ is chloride, bromide, methosulfate, ethosulfate, nitrate or tosylate.

Non-limiting examples of monoalkyl quats are:

cetyltrimethylammonium chloride (C16);
stearyltrimethylammonium chloride (C18);
behenetrimethylammonium chloride (C22);
cetrimonium bromide (C16);
soytrimonium chloride (C18);
tallowtrimonium chloride (C18);
behentrimethylammonium methosulfate (C22);
Peg-2 Olealmonium chloride (C18);
palmityltrimethylammonium chloride (C16);
hydrogenated tallowtrimethylammonium chloride (C18);
hydrogenated tallowtrimethylammonium bromide (C18);
hydrogenated tallowtrimethylammonium methosulfate (C18);
cetrimonium tosylate (C16): and
eicosyltrimethylammonium chloride (C20), Dialkyl quats can be compounds of the formula $NR^5R^6R^7R^8X^-$ wherein $R^5$ and $R^6$ are C1–C3 alkyl groups and $R^7$ and $R^8$ are C20–C22 alkyl groups; and X⁻ is chloride, bromide, methosulfate, ethosulfate, nitrate, acetate, phosphate; or tosylate.

Non-limiting examples of dialkyl quats are:

di(partially hardened soyethyl) hydroxyethylmonium methosulfate (C20);
dieicosyldimethylammonium methosulfate (C20);
didocosyldimethylammonium chloride (C22);
didocosyldimethylammonium methosulfate (C22);
didocosyldimethylammonium bromide (C22);
diheneicosyldimethylammonium chloride (C21)

The following are non-limiting examples of fatty alcohols which may be used in the compositions of the invention:

cetyl alcohol;
stearyl alcohol;
cetearyl alcohol;
behenyl alcohol; and
arachidyl alcohol.

Optional ingredients which may be included in the compositions of the invention are hydrocarbons such as paraffin, vaseline solid paraffin, squalene, oligomer olefins and the like; amidoamines such as stearamidopropyl dimethylamine, isostearamidoethyl morpholine, behenamidopropyl dimethylamine and the like; humectants such as glycerine, propylene glycol, glycerol, sorbitol and the like; esters, such as isopropyl palmitate, isopropyl myristate, and stearyl stearate and the like; emulsifiers such as glyceryl monostearate, sorbitan monopalmitate, polyoxyethylene stearate and the like; cellulose derivatives such as hydroxypropylcellulose; cationic cellulose, hydroxyethyl cellulose and the like; thickening agents such as natural polymers and the like; and other ingredients such as solvents, bacteriocides, colors, and fragrances.

Compositions of the invention may be prepared by methods which are known to those skilled in the art. Ingredients used in the preparation of compositions of the invention are either known or may be prepared by known methods.

Compositions of the invention are used to condition hair by first wetting the hair, applying the composition of the invention, lathering the hair, and then rinsing the hair. Alternatively, water and conditioner may be applied to the hair simultaneously. Conditioning with compositions may be done right after shampooing when the hair is still wet. Alternatively, conditioning the hair may be done separately from shampooing.

Compositions of the invention provide unexpectedly superior conditioning benefits when compared with prior art formulations. Compositions of the invention provide unexpectedly provide a high, consumer acceptable viscosity using relatively low levels of monoalkyl quat, dialkyl quat, and fatty alcohol.

Finally, compositions of the invention provide unexpectedly superior conditioning without the use of increased fatty alcohols.

Composition (A) of the invention can be prepared with ingredients in the following amounts expressed as wt. %'s.

| Ingredients | Composition (A) |
|---|---|
| Cetrimonium Chloride, 30% active | 2.8 |
| Didocosyldimethylammonium Chloride 100% active | .21 |
| Cetyl Alcohol, 100% active | 3.0 |
| Other[1] | q.s. |

Other[1] is soft water, fragrances, preservatives and other minor ingredients.

The compositions of the invention will show the following improved attributes: conditioning performance, deposition, and viscosity, at low total solid levels. This could be shown by Instron wet combing testing, salon testing, and Brookfield viscosity measurements.

What is claimed is:

1. An opaque hair conditioning composition comprising:

(a) a monoalkyl quat having 16 to 22 carbon atoms in each alkyl substituent;

(b) a dialkyl quat having 20 to 22 carbon atoms in each alkyl substituent: and (c) a fatty alcohol in an amount of about 1% to about 4% wherein the ratio of (a) to (b) is about 4:1 to about 20:1.

2. A composition according to claim 1 wherein the ratio of (a) to (b) is about 4:1 to about 10:1.

3. A composition according to claim 2 wherein the ratio of (a) to (b) is about 4:1 to about 5:1.

* * * * *